(12) United States Patent
Sforza et al.

(10) Patent No.: US 10,842,613 B2
(45) Date of Patent: Nov. 24, 2020

(54) DEVICES AND METHODS FOR IMPLANTATION PROCEDURES

(71) Applicant: Establishment Labs S.A., Alajuela (CR)

(72) Inventors: Marcos Sforza, Birmingham (GB); Juan José Chacón Quirós, Alajuela (CR); Nicole Martínez, Alajuela (CR); Nathalia Araujo, Alajuela (CR); Roberto De Mezerville, Alajuela (CR)

(73) Assignee: Establishment Labs, S.A., Alajuela (CR)

( * ) Notice: Subject to any disclaimer, the term of this patent is extended or adjusted under 35 U.S.C. 154(b) by 140 days.

(21) Appl. No.: 16/136,400

(22) Filed: Sep. 20, 2018

(65) Prior Publication Data

US 2019/0083234 A1 Mar. 21, 2019

Related U.S. Application Data

(60) Provisional application No. 62/561,359, filed on Sep. 21, 2017.

(51) Int. Cl.
*A61F 2/12* (2006.01)
*A61M 5/32* (2006.01)
*A61B 17/34* (2006.01)

(52) U.S. Cl.
CPC ............... *A61F 2/12* (2013.01); *A61M 5/32* (2013.01); *A61M 5/3286* (2013.01); *A61B 17/3421* (2013.01); *A61B 17/3468* (2013.01); *A61B 2017/3454* (2013.01); *A61B 2017/3456* (2013.01)

(58) Field of Classification Search
CPC ........................................................ A61F 2/12
USPC ......................................................... 623/7–8
See application file for complete search history.

(56) References Cited

U.S. PATENT DOCUMENTS

| 4,642,101 A | 2/1987 | Krolikowski et al. |
| 6,524,296 B1 | 2/2003 | Beals |
| 8,632,498 B2 | 1/2014 | Rimsa et al. |
| 2001/0041936 A1* | 11/2001 | Corbitt, Jr. ............... A61F 2/12 623/8 |
| 2008/0027541 A1* | 1/2008 | Gerut ................. A61B 18/148 623/8 |

(Continued)

FOREIGN PATENT DOCUMENTS

CN 203263945 11/2013

*Primary Examiner* — Suzette J Gherbi
(74) *Attorney, Agent, or Firm* — Bookoff McAndrews, PLLC (57) ABSTRACT

Devices and methods of treatment useful in implantation and post-implantation procedures are described. The devices and methods may be used to correct deformities and/or asymmetries in tissues near an implant, support tissues near an implant, and/or refine the shape of an area of the body after placement of an implant, for example. The method may include inserting a cannula into tissue adjacent to or near an implant of a patient, and delivering fat or other filler material(s) to the tissue, wherein the cannula is configured to prevent or otherwise minimize the risk of damaging the implant, e.g., a breast implant. The cannula may include an elongate member having a lumen therein, an atraumatic distal tip, and an opening disposed proximal to the distal tip, the opening being in fluid communication with the lumen for delivering the fat or other filler material(s).

5 Claims, 6 Drawing Sheets

(56) References Cited

U.S. PATENT DOCUMENTS

| | | | |
|---|---|---|---|
| 2013/0325120 A1* | 12/2013 | McClellan | A61F 2/12 623/8 |
| 2014/0100426 A1* | 4/2014 | Barbour | A61M 5/3286 600/178 |
| 2014/0221732 A1* | 8/2014 | Dayton | A61B 90/02 600/30 |
| 2014/0257179 A1* | 9/2014 | Schwab | A61M 5/3156 604/82 |
| 2017/0007738 A1* | 1/2017 | Leisk | A61L 27/56 |
| 2017/0021066 A1* | 1/2017 | Sforza | A61M 1/008 |
| 2017/0042664 A1* | 2/2017 | Corbitt, Jr. | A61F 2/0059 |
| 2017/0232148 A1* | 8/2017 | Nguyen | A61L 27/26 514/180 |
| 2017/0258574 A1* | 9/2017 | Hutmacher | A61F 2/12 |

* cited by examiner

DEVICES AND METHODS FOR IMPLANTATION PROCEDURES

CROSS-REFERENCE TO RELATED APPLICATIONS

This application claims priority to U.S. Application No. 62/561,359 filed on Sep. 21, 2017, which is incorporated by reference herein in its entirety.

TECHNICAL FIELD

The present disclosure generally relates to devices used during breast implant procedures, including devices used for injecting fat adjacent to a breast implant that reduce the risk of damaging the implant.

BACKGROUND

Many people have medical implants for medical and/or aesthetic purposes. For example, mammary implantation is a common medical/aesthetical procedure in many parts of the world. Often, women who have suffered from breast cancer or mammary hypoplasia (for example due to a lack of, or damage to, mammary tissue) opt for breast implants.

After such implantations, often with silicone gel filled implants, there is a still further need to refine or supplement the shape of the breast to correct any remaining deformities or asymmetries. In such cases, superficial breast reconstructions, such as fat grafting, are available. During fat grafting, the surrounding breast area is enlarged or filled by injecting fat through an incision via a cannula. The cannula opens a channel as it is inserted through the incision, and when it is pulled back the fat is released fulfilling the opened spaces. However, care must be taken to avoid contacting an outer surface of the breast implant with a sharp distal end of the cannula, as doing so could endanger the integrity of the implant. Such contact could provoke health and aesthetic risks, among other risks, by puncturing or scarring the implant shell, causing it to rupture. Current procedures are often performed without visualization of the cannula at the delivery site, and thus, after current fat injection procedures, a post-operative ultrasound image is usually required to inspect the integrity of the implant and ensure that it was not damaged during the injection.

SUMMARY

In some aspects, the present disclosure is directed to methods of treating a patient. The method may include inserting a cannula into subglandular tissue adjacent to a breast implant of the patient, the cannula including a member having a lumen therein, an atraumatic distal tip, and an opening disposed proximal to the distal tip, the opening being in fluid communication with the lumen, and delivering a biocompatible filler material, through the lumen and the opening, to the subglandular tissue, wherein the cannula is configured to apply at least 25 N of compressive force, such as from 25 N to about 40 N of compressive force, to a shell of the breast implant that encloses a gel or liquid without puncturing the shell.

Inserting the cannula may include positioning the distal tip of the cannula within about 30 mm, e.g., about 0.1 mm to about 10 mm, from the shell of the breast implant. In some examples herein, the biocompatible filler material is not delivered into a tissue pocket that contains the breast implant. In some examples, inserting the cannula may include directly contacting the shell of the breast implant with the distal tip without damaging the breast implant.

The distal tip of the cannula may be hollow or solid. For example, the distal tip may be ovoid in shape and hollow. In some examples, the distal tip may be ovoid in shape and solid. Additionally or alternatively, the distal tip may have a maximum diameter ranging from about 2.0 mm to about 5.0 mm, such as from about 4.0 mm to about 5.0 mm. At least a portion of the cannula may include a lubricious coating. According to some aspects of the present disclosure, the member of the cannula may be formed from a first material, and the distal tip may be formed from a second material, wherein the second material has a lower durometer than the first material. In some examples, the member and the distal tip may comprise the same material or materials. In at least one example, the opening may have a length ranging from 2.0 mm to 3.0 mm and a width ranging from 0.5 mm to 1.5 mm.

According to some aspects of the present disclosure, the shell of the breast implant may enclose a silicone gel or saline liquid, the shell having a thickness ranging from about 0.1 mm to about 1.2 mm. In some examples, the shell of the breast implant may have a thickness ranging from 0.3 mm to 0.6 mm. Further, for example, the shell of the breast implant may enclose a silicone gel having a penetration value ranging from 5.0 mm to 8.0 mm. In at least one exemplary method, the biocompatible filler material may comprise fat that is autologous to the patient, and wherein an amount of fat delivered to the subglandular tissue ranges from about 5 mL to about 500 mL. In some examples, delivering the biocompatible filler material to the subglandular tissue may include delivering a first volume of the biocompatible filler material to a first location proximate the breast implant and delivering a second volume of the biocompatible filler material to a second location proximate the breast implant different from the first location.

The present disclosure further includes a method treating a patient by inserting a cannula into tissue adjacent to a breast implant, the cannula including a member having a lumen therein, an atraumatic, ovoid, distal tip having a maximum diameter ranging from about 3 mm to about 4 mm, and an opening disposed proximal to the distal tip, the opening being in fluid communication with the lumen and having a length ranging from 2.2 mm to 2.7 mm and a width ranging from 1.0 mm to 1.5 mm. Inserting the cannula may include directly contacting a shell of the breast implant without puncturing the breast implant, the shell having a thickness of less than 1.0 mm and enclosing a silicone gel, and delivering fat, autologous to the patient, through the member and the opening, into the tissue.

The method may include creating an umbilical, axillary, breast fold, or areolar incision in the patient, and delivering the breast implant to a submuscular or subglandular pocket via the incision, wherein the cannula is inserted into the tissue via the incision after delivering the breast implant. The cannula can also be inserted from independent new incisions in the skin on the breast. In at least one example, the fat is not delivered into the submuscular or subglandular pocket that contains the breast implant. In some examples, the member of the cannula may have an outer diameter ranging from 1.5 mm to 2.5 mm.

The present disclosure further includes a method treating a patient by creating an umbilical, axillary, breast fold, or areolar incision in the patient, delivering a breast implant to a submuscular or subglandular pocket via the incision, inserting a cannula into tissue adjacent to the breast implant, the cannula including a member having a lumen therein, the member having an outer diameter ranging from 2.0 mm to 2.5 mm and an inner diameter ranging from 1.0 mm to 1.5 mm, an atraumatic, ovoid, distal tip having a maximum diameter greater than the outer diameter of the member, and an opening disposed proximal to the distal tip, the opening being disposed in a circumferential side surface of the member and in fluid communication with the lumen. In some examples, inserting the cannula may include directly contacting a shell of the breast implant without puncturing the breast implant, the shell having a thickness ranging from 0.3 mm to 0.6 mm and enclosing a silicone gel. The method may include delivering fat, autologous to the patient, through the member and the opening, into the tissue, wherein the fat is not delivered into the submuscular or subglandular pocket that contains the breast implant.

The various examples provided herein, including the examples above, serve to illustrate various aspects of the present disclosure, and should not be interpreted as the only examples or embodiments contemplated herein. It is to be understood that the above examples and/or portions thereof may be combined and/or interchanged with one another. Additional examples, embodiments and advantages will be set forth in part in the description which follows, including variations and alternatives of the examples provided according to the general principles provided herein, which may be understood from the description and/or may be learned by practice of the disclosure based on the guidance herein.

BRIEF DESCRIPTION OF THE FIGURES

The accompanying drawings, which are incorporated in and constitute a part of this specification, illustrate various examples and together with the description, serve to explain the principles of the present disclosure. Any features of an embodiment or example described herein (e.g., device, method, etc.) may be combined with any other embodiment or example, and are encompassed by the present disclosure.

DETAILED DESCRIPTION

Aspects of the present disclosure are described in greater detail below. The terms and definitions as used and clarified herein are intended to represent the meaning within the present disclosure. The terms and definitions provided herein control, if in conflict with terms and/or definitions incorporated by reference.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value.

As used herein, the term "posterior" refers to the backside of a patient, and the term "anterior" refers to the front of a patient. Thus, the posterior side of a breast implant is the side of the implant facing the chest wall, while the anterior side is the opposite side closest to the skin. Similarly, the posterior side of a gluteal or buttock implant is the side closest to the skin, and the anterior side is the opposite side facing the pelvis. As used herein, the term "proximal" refers to a direction or location closer to a patient (e.g., the posterior side of a breast implant closest to the chest wall), whereas the term "distal" refers to a direction or location farther from the patient (e.g., the anterior surface of a breast implant closest to the skin).

Although aspects of the present disclosure may be described in the context of a given type of medical implant, such as, for example, a breast implant or prosthesis, embodiments of the present disclosure may be, and/or may be applied to, a variety of medical implants and instruments. Non-limiting examples include, e.g., gluteal implants, calf implants, testicular implants, penile implants, and other body contour implants, electro-stimulation implants (e.g., pacemakers, spinal cord stimulators), drug delivery reservoirs, implantable catheters, indwelling catheters, injection ports, drug delivery ports, gastric balloons, and gastric bands.

Figure 1:
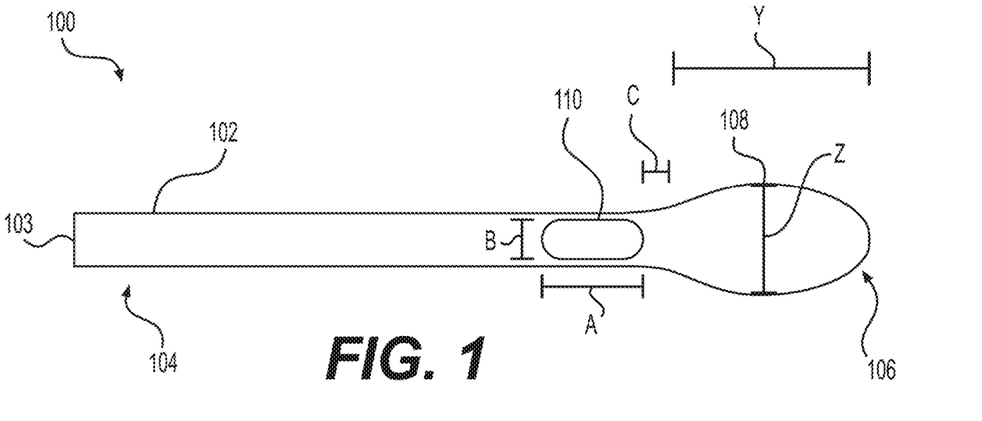
FIG. 1 is a partial side view of a cannula, according to an aspect of the present disclosure.

An exemplary cannula 100 according to some aspects of the present disclosure is shown in FIG. 1, and includes an elongate member 102 extending from a proximal end 103 toward a distal end 106. Cannula 100 may include a distal tip 108 at distal end 106, and an opening 110 disposed proximal to distal tip 108.

Elongate member 102 may be a needle, shaft, catheter, tube, or other suitable elongate member. A lumen may extend through elongate member 102 to allow for the transfer of filling material (e.g., fat or dermal filler) from the proximal end of cannula 100, through the lumen, and out of opening 110 proximate distal tip 108. In some examples, elongate member 102 may comprise a biocompatible metal or metal alloy, such as titanium, stainless steel (e.g., Type 305 stainless steel), or another suitable metal or alloy. In other examples, elongate member 102 may comprise one or more other biocompatible materials, such as, e.g., polyethylene, including high-density polyethylene (HDPE), silicone, polyurethane, ethylene tetrafluoroethylene (ETFE), poly(styrene-block-isobutylene-block-styrene) (SIBS), or any other suitable medical grade polymers or copolymers. In yet other examples, elongate member 102 may comprise a combination of materials, e.g., a combination of biocompatible metals, metal alloys, polymers, and/or copolymers such as the materials listed above. Elongate member 102 may be substantially rigid, or may be at least partially flexible and configured to extend through tortuous anatomy.

Cannula 100 may be formed in any suitable dimensions. For example, elongate member 102 may have a length ranging from about 3 cm to about 30 cm, such as from about 5 cm to about 25 cm, or from about 10 cm to about 20 cm, e.g., about 15 cm. Further, for example, elongate member 102 may have an outer diameter (OD) ranging from about 0.7 mm to about 5.0 mm, such as from about 1.5 mm to about 4.5 mm, from about 1.5 mm to about 3.0 mm, or from about 2.5 mm to about 3.5 mm, e.g., an OD of about 1.0 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 3.0 mmab, about 3.5 mm, about 4.0 mm, about 4.5 mm, or about 5.0 mm; and an inner diameter (ID) ranging from about 0.5 mm to about 4.9 mm, such as from about 1.0 mm to about 3.0 mm, or from out 1.20 mm to about 1.46 mm, e.g., an ID of 0.5 mm, about 0.7 mm, about 1.0 mm, about 1.1 mm, about 1.2 mm, about 1.3 mm, about 1.33 mm, about 1.4 mm, about 1.5 mm, about 1.6 mm, about 1.7 mm, about 1.8 mm, about 1.9 mm, about 2.0 mm, about 2.5 mm, about 3.0 mm, about 3.5 mm, about 4.0 mm, about 4.5 mm, or about 4.9 mm. Elongate member 102 and/or other portions of cannula 100 may be reusable and/or disposable.

Distal tip 108 may have an atraumatic shape configured to substantially reduce or prevent trauma to tissues and/or objects that come into contact with distal tip 108. In the examples shown in FIGS. 1-3, distal tip 108 is shown with a rounded, bulbous shape. In some examples, distal tip 108 may be oval or ovoid in shape, e.g., egg-shaped. Thus, distal tip 108 may have a varying diameter along its length. The maximum diameter of distal tip 108 may range from about 1.0 mm to about 1.0 cm, such as from about 1.0 mm to about 7.5 mm, from about 1.5 mm to about 7.5 mm, from about 5.0 mm to about 7.0 mm, from about 2.2 to about 3.5, or from about 3.0 mm to about 4.0 mm, e.g., a maximum diameter of about 3.0 mm, 3.1 mm, 3.2 mm, 3.3 mm, 3.4 mm, 3.5 mm, or 3.6 mm. In at least one example, distal tip 108 may have a maximum horizontal diameter (measured along a y-axis, perpendicular to the x-axis along the cannula length, labeled "Y" in FIG. 1) ranging from about 1.0 mm to about 5.0 mm, such as from about 3.3 mm to about 3.5 mm or from about 4.0 mm to about 5.0 mm, e.g., about 4.3 mm, about 4.4 mm, about 4.5 mm, or about 4.6 mm; and a maximum vertical diameter (measured along a z-axis perpendicular to the x-axis and y-axis, labeled "Z" in FIG. 1) ranging from about 1.0 mm to about 5.0 mm, such as from about 2.0 mm to about 3.0 mm, or from about 2.2 mm to about 2.4 mm, e.g., about 2.3 mm.

For example, beginning from the proximal end of distal tip 108 and travelling distally, distal tip 108 may have an increasing diameter until a widest diameter is reached. Distal tip 108 may have a decreasing diameter in a distal direction away from the widest diameter of the distal tip 108 to form a rounded end at distal end 106 (i.e., the distalmost portion of distal tip 108). It is also contemplated that distal tip 108 may include other suitable atraumatic shapes. For example, distal tip 108 may be substantially spherical (e.g., a ball tip). In at least one example, distal tip 108 may have a length (measured along the x-axis, i.e., proximal to distal direction) ranging from about 2.0 mm to about 3.0 cm, such as from about 1.0 cm to about 2.0 cm, or from about 1.2 cm to about 1.6 cm.

Figure 2:
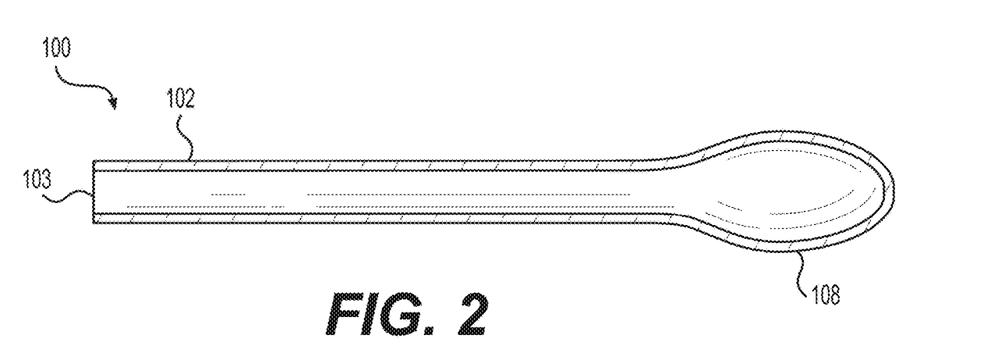
FIG. 2 is a partial side cross-sectional view of the cannula of FIG. 1.
Figure 3:
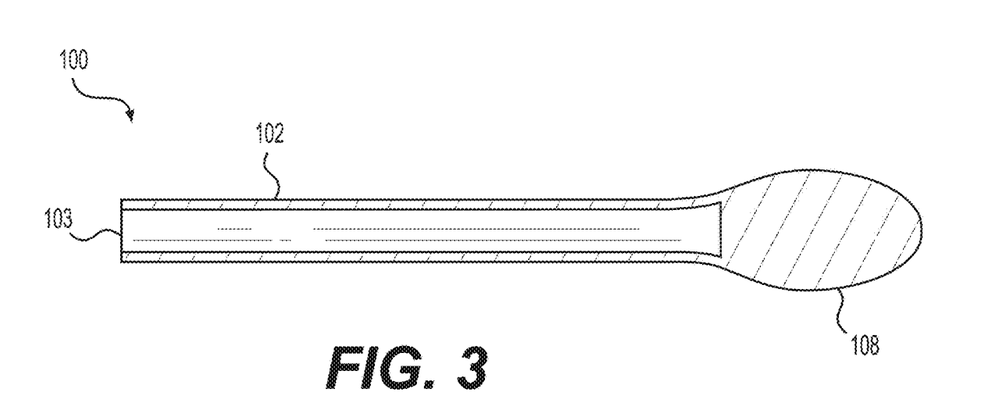
FIG. 3 is a partial side cross-sectional view of an alternative embodiment of the cannula of FIG. 1.

Distal tip 108 may be hollow (see, e.g., FIG. 2) or solid (see, e.g., FIG. 3). In some examples, the distalmost portion of distal tip 108 may be closed (e.g., the distalmost portion being solid or separated from the remainder of cannula 100 by a wall or other barrier) such that no material may travel through it. Since opening 110 of the cannula 108 may be used to inject the material (e.g., fat or dermal filler), a solid tip may allow the material to exit opening 110 directly when it reaches a distalmost end of the cannula lumen. When distal tip 108 is solid, it may be formed of substantially the same material as a remainder of cannula 100, or may include one or more different materials. When distal tip 108 is hollow, an amount of the material (e.g., a small percentage of fat or dermal filler) may fill a cavity of a hollow distal tip 108, e.g., remaining trapped in distal tip 108. Thus, in some examples, residual material may remain inside of a hollow distal tip 108, which could be difficult to remove. Thus, if cannula 100 is intended for reuse, it should be properly sterilized to reduce or eliminate the risk of contamination during a subsequent use.

In alternative embodiments, the distalmost portion distal tip 108 may include an opening in communication with the cannula lumen, e.g., for the passage of fluid, fat, tools, or the like.

Distal tip 108 may comprise the same material or materials as a remaining portion of cannula 100, e.g., the same material or materials as elongate member 102. However, it is also contemplated that distal tip 108 may comprise different material(s). For example, distal tip 108 may comprise a harder or softer material than elongate member 102. In some examples, distal tip 108 may be formed from a material having a lower Mohs hardness or Shore hardness than the material that forms elongate member 102. For example, elongate member 102 may be formed from a metal such as stainless steel, while distal tip 108 is formed from a polymer material, such as, e.g., a polyurethane elastomer or other suitable material(s) having a lower hardness value. Any combination of biocompatible materials suitable for elongate member 102 and distal tip 108 may be used. In some examples, distal tip 108 may be formed from the same material as elongate member 102, but may be coated with a softer material. In some examples, distal tip 108 may be semi-rigid or flexible, e.g., comprising a polymer or copolymer that flexes when contacting tissue, a medical implant, or other devices or tools during a medical procedure.

In some examples, the surface of cannula 100 proximal to distal tip 108 that defines opening 110 may have relatively sharp edges, as discussed below. When distal tip 108 inadvertently contacts the outer surface of an implant during, e.g., a fat grafting procedure, the atraumatic shape of distal tip 108 and/or the distance of opening 110 from the distal end 106 of cannula 100 may help to block the sharp edges surrounding opening 110 from contacting the outer surface the implant. This may help avoid ruptures, abrasions, punctures, and/or tears that could endanger the integrity of the implant (or surrounding organs and tissues), during the injection of material into the surrounding area. In some examples, the shape of distal tip 108 may prevent damage to an implant regardless of the angle of contact, and how much the distal tip 108 causes the outer surface of the implant to deform.

Elongate member 102 and/or distal tip 108 may have a smooth outer surface to assist in insertion into tissue during a medical procedure. In some examples, elongate member 102 and/or distal tip 108 may include a lubricious, hydrophilic coating, or a lubricant, configured to reduce friction forces between cannula 100 and tissues and/or a breast implant in vivo. The lubricious coating or lubricant may allow elongate member 102 and/or distal tip 108 to slide against an inserted implant to help prevent elongate member 102 and/or distal tip 108 from snagging, puncturing, tearing, or otherwise damaging the surface of the implant inserted into the body of a patient. The lubricious coating may comprise any suitable biocompatible material such as, e.g., polytetrafluoroethylene (PTFE), polyvinylpyrrolidone (PVP), silicone, or the like.

Opening 110 may be disposed though a circumferential side surface of elongate member 102, e.g., proximal to distal tip 108. Opening 110 may be in fluid communication with the lumen of elongate member 102 to allow for the passage of materials through the lumen to exit opening 110 into the body of a patient. As shown in FIG. 1, opening 110 has a curved boundary or periphery such that opening 110 is generally oval in shape, or rectangular with rounded corners, but other suitable shapes, such as, e.g., circular, are also contemplated. According to some aspects of the present disclosure, opening 110 may have length A along the x-axis and a width B along the y-axis (e.g., A and B corresponding the diameter for a circular opening (A=B), or A and B being large and small diameters for an oval opening or the length and width of a rounded rectangular opening (A>B or B>A)) each ranging from about 0.5 mm to about 4.0 mm, such as from about 1.0 mm to about 4.0 mm, such as from about 1. from about 1.5 mm to about 3.5 mm, from about 2.0 mm to about 3.0 mm, or from about 2.2 mm to about 2.5 mm. For example, opening 110 may have a length A of about 2.0 mm, about 2.1 mm, about 2.2 mm, about 2.3 mm, about 2.4 mm, about 2.5 mm, about 2.6 mm, about 2.7 mm, about 2.8 mm, about 2.9 mm or about 3.0 mm; and a width B of about 2.0 mm, about 2.1 mm, about 2.2 mm, about 2.3 mm, about 2.4 mm, about 2.5 mm, about 2.6 mm, about 2.7 mm, about 2.8 mm, about 2.9 mm or about 3.0 mm. In at least one example, opening 100 may be a rounded rectangle having a length A ranging from about 1.0 mm to about 8.0 mm, such as from about 2.0 mm to about 6.0 mm, or from about 2.5 mm to about 5.5 mm, e.g., a length A of about 2.2 mm, about 2.5 mm, or about 2.7 mm; and a width B ranging from about 1.0 mm to about 4.0 mm, or from about 2.0 mm to about 3.0 mm, e.g., a width B of about 1.0 mm, about 1.2 mm, or about 1.4 mm.

In some examples, the surfaces of elongate member 102 that define the periphery of opening 110 may be smoothed to reduce the potential for those surfaces to cause trauma to tissue or to an implant. For example, after opening 110 is formed through the circumferential side surface of elongate member 102, the peripheral surfaces defining the opening may be abrupt and relatively sharp. In some examples, those surfaces may be smoothed by a suitable tool, e.g., a rotary tool, a file, a polishing tool, etc.

The location of opening 110 relative to distal tip 108 and distal end 106 may be selected to minimize contact between the portion of elongate member 102 defining opening 110 and the surface of an implant. For example, opening 110 may be located sufficiently proximal to distal tip 108 and/or distal end 106 such that when cannula 100 is advanced in the area of an implant, distal tip 108 is the only feature of cannula 100 that touches the surface of the implant. Thus, for example, the distal edge of opening 110 may be spaced from the distal end 106 by a distance (labeled "C" in FIG. 1) approximately equal to the length of the distal tip 108, or within about 0.05 mm to about 0.1 mm of the proximal end of the distal tip 108, such as within about 0.09 mm to 0.70 mm of the proximal end of distal tip 108. For example, the distal edge of opening 110 may be located from about 5.0 mm to about 4.5 cm from the distal end 106 of cannula 100, such as from about 1.0 cm to about 3.0 cm, or from about 1.5 cm to about 2.5 cm. In some examples, the distance between opening 110 and the proximal-most end of distal tip 108 may range from 0 cm to about 1.5 cm, such as from about 0.5 cm to about 1.2 cm, or from about 0.7 cm to about 1.0 cm.

The proximal end 103 of elongate member 102 may include an adapter such as, e.g., a Luer lock or other adapter, for coupling cannula 100 to a delivery member and/or a source of material for injection. In some examples, the delivery member includes a syringe that is manually actuated to deliver material, e.g., fat, through the elongate member 102 and into the patient. In other examples, a syringe (including syringes suitable for manual actuation) or other suitable container may be coupled to a pump that is configured to drive fat or other material through elongate member 102 electronically. For example, the syringe or other suitable container may be coupled to a pump controlled by a suitable controller. The pump may be any suitable pump, such as, e.g., a peristaltic pump, piston pump, motorized pump, microfluidic pump, infusion pump, or the like.

Implants suitable for the present disclosure may include any of the features or combination of features of implants disclosed in U.S. application Ser. No. 13/412,221 (published as US 2012/0232652 A1); U.S. application Ser. No. 14/028,193 (published as US 2014/0081398 A1); U.S. application Ser. No. 14/679,788 (published as US 2015/0282926 A1); U.S. Provisional Application No. 62/334,667 filed on May 11, 2016; and/or U.S. Provisional Application No. 62/410,121 filed on Oct. 19, 2016, each incorporated by reference herein.

Exemplary implants of the present disclosure may include a shell that encloses or surrounds a fluid or gel filling. The shell may comprise a single-layer or may be multi-layered, and may be formed from one or more biocompatible materials suitable for the implant. The shell may comprise a patch or other material that closes an opening useful for introducing the filling into the implant. The implant may have a variety of shapes and sizes suitable for implantation in the body. For example, the implant may be a breast implant having a size and shape suitable for implantation during a breast augmentation or reconstruction surgery.

The shell may be flexible, e.g., the shell comprising an elastic material. In some examples, the shell may comprise a series of successive layers of silicone, which may be cross-linked or otherwise attached together. One or more layers of the shell may comprise, for example, one or more siloxane polymer elastomers, such as, e.g., diphenyldimethyl polysiloxane polymer and/or vinyl-functional silicone polymer. When the shell comprises multiple layers, each layer may have the same or different compositions and/or elasticity characteristics. For example, polymer or copolymer dispersions with different viscosities may be used to prepare the layers of a multilayered shell, e.g., by dip-molding or other suitable manufacturing process. The thickness of the shell may range from about 0.1 mm to about 1.2 mm, such as from about 0.2 mm to about 0.8 mm, from about 0.3 mm to about 1.1 mm, or from about 0.4 mm to about 0.6 mm. In some examples, the thickness of the shell may range from about 0.33 mm to 1.02 mm, e.g., a thickness of about 0.4 mm, about 0.5 mm, about 0.6 mm, about 0.7 mm, about 0.8 mm, about 0.9 mm, or about 1.0 mm. The outermost surface of the shell may have a surface texture, such as the surface textures described in U.S. Provisional Application No. 62/334,667 filed on May 11, 2016, and/or U.S. Provisional Application No. 62/410,121 filed on Oct. 19, 2016, each incorporated by reference herein.

In some examples, the shell may provide for at least +200% elongation when measured using a tensile testing system (e.g., an Instron® static tensile testing system having a charged cell of 50 N). For example, the shell may exhibit elongation values ranging from about 450% to about 750%, such as from about 500% to about 750%, or from about 650% to about 750%. The elongation value may comply with breast implant standard 14607 of the International Organization for Standardization.

The filling of the implant may comprise any material or combination of materials suitable for an implant. For example, in a breast prosthesis, the filling may comprise a biocompatible liquid or gel filler material, such as a saline liquid or a silicone gel. The silicone may have a relatively high elasticity and/or a relatively low viscosity, and may be, e.g., a visco-elastic silicone material. In some examples, the implant may comprise a silicone gel with a penetration value ranging from about 10 to about 80 1/10 mm (corresponding to about 1.0 mm to about 8.0 mm) as measured by a penetrometer, such as from 10 to 60 1/10 mm (1.0 mm to 6.0 mm), from 20 to 50 1/10 mm (2.0 mm to 5.0 mm), from 20 to 70 1/10 mm (2.0 mm to 7.0 mm), from 25 to 55 1/10 mm (2.5 mm to 5.5 mm), from 30 to 50 1/10 mm (3.0 mm to 5.0 mm), from 20 to 35 1/10 mm (2.0 mm to 3.5 mm), from 50 to 80 1/10 mm (5.0 mm to 8.0 mm), from 50 to 60 1/10 mm (5.0 mm to 6.0 mm), or from 70 to 80 1/10 mm (7.0 mm to 8.0 mm). The penetration value is a factor that measures the firmness of a colloid, such as a silicone gel, wherein lower values indicate more cohesion and lower values indicate less cohesion.

The devices disclosed herein may be used in a medical procedure, such as, e.g., a procedure to assist in correcting deformities and/or asymmetries in tissues near an implant, supporting tissues near an implant, and/or refining the shape of an area of the body after placement of an implant. For example, the procedure may include injection of fat or other biocompatible material(s) into tissue next to or near to an implant after the implant has been inserted. Exemplary biocompatible materials may include fat or other biological materials obtained from the patient (e.g., autologous or autogeneic materials) or from another human or non-human source (e.g., allogeneic or xenogeneic materials), other suitable filler materials such as collagen, hyaluronic acid, and other biocompatible materials, and any combinations thereof. Referring to FIGS. 1-3 discussed above, cannula 100 may be used to inject the biocompatible material(s) into tissue while avoiding damage to the implant.

Figure 4:
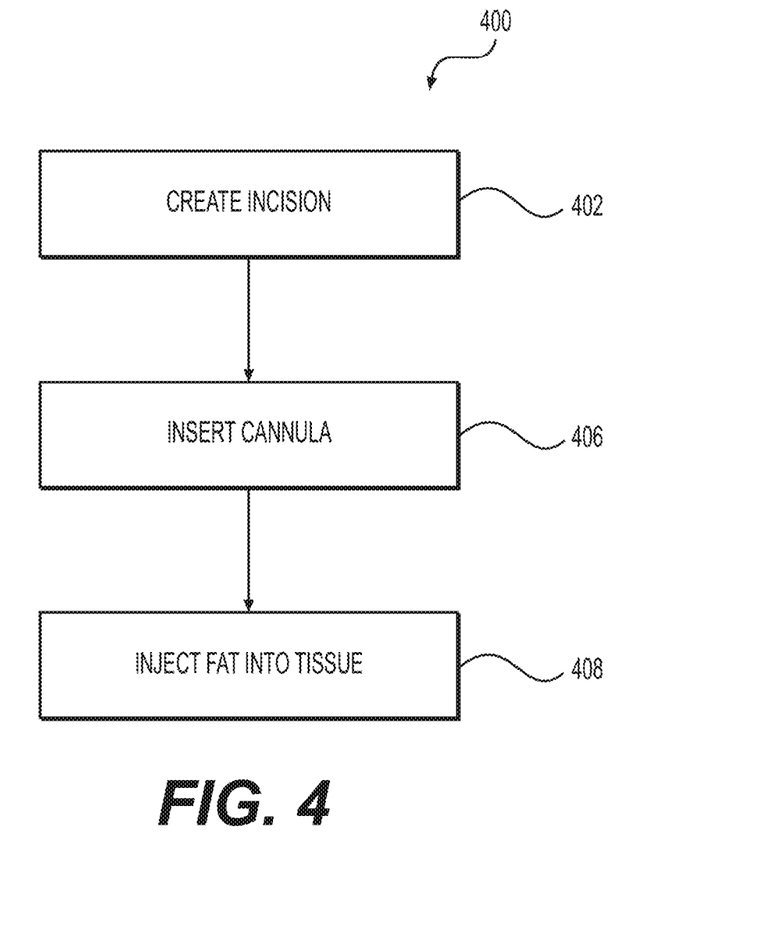
FIG. 4 is a flow chart of a method according to an aspect of the present disclosure.

FIG. 4 shows a method 400 according to an example of the present disclosure. The method 400 may begin at step 402, where a physician or other healthcare provider may create an incision in the body of a patient to access an area adjacent to an implant, such as a breast implant. In some cases, a relatively larger incision may be used to accommodate the distal tip of a cannulas according to the present disclosure, as compared to smaller sized incisions used for cannulas without a rounded, bulbous-shaped tip. The incision may be formed in any suitable location to create access to the areas surrounding the breast implant. In some examples, the incision at step 402 may be made in a separate procedure from the breast implant procedure, e.g., after completion of the breast implant procedure. For example, the incision at step 402 may be made one day, one week, one year, or after an even longer period of time after completion of the breast implant procedure.

Additionally or alternatively, step 402 may occur during the initial breast implantation procedure. For example, the cannula may be inserted into the same incision used to insert the breast implant and/or one or more other incision sites. For example, in some procedures, an incision may be made in the umbilicus for insertion of a breast implant. A blunt dissecting instrument may be introduced to make the incision, over which a larger cannula or tube is inserted and advanced to the tissue pocket where the breast implant is to be positioned. The incision may be manipulated by retractors and/or tissue-spreaders to expand and hold open the incision site to allow for the physical manipulation of the implant into the tissue pocket. Other incision and implantation approaches that may be used include, e.g., an axillary endoscopic approach (incision in the first axillary crease), a breast fold approach, and an areolar approach. A pocket for placement of the implant also may be formed during the procedure. The pocket may be a subglandular pocket or a submuscular pocket, for example. A subglandular pocket may be disposed behind the breast gland and in front of or on top off the pectoralis muscle. A submuscular pocket may be disposed behind or underneath the pectoralis muscle.

After the implant is inserted into the pocket (e.g., immediately after insertion, or a period of time after the implantation procedure), there may be a further need to refine or supplement the shape of the breast to correct any remaining deformities or asymmetries during the procedure and/or after the initial implantation procedure. In these cases, superficial breast reconstructions, such as fat grafting, are available. The injected fat may have been previously collected from a different area or body part of the same patient, such as, e.g., from the hip area, stomach, leg, or buttocks of the patient. During a fat harvesting portion of the method, any suitable harvesting cannula may be utilized. The injected fat may be autologous fat or laboratory-cultured fat.

Thus, the method may proceed to step 406, where cannula 100 is inserted into the patient through an incision. The incision may be a different incision than the one used to insert the implant into the pocket. It also contemplated that in some examples, the cannula 100 may be inserted through the same incision used to insert the implant into the pocket. In some examples, during the inward movement of cannula 100, a tunnel may be created that will be filled when cannula 100 is withdrawn. The blunt nature of distal tip 108 of cannula 100 may result in separation of subcutaneous tissue by blunt dissection, and not by cutting, potentially reducing tissue trauma (e.g., bleeding or damage to fat cells). Because this tunnel is ultimately filled with fat, after completion of the procedure, a smaller portion of the tunnel will be filled with blood and clot deposits, resulting in reduced trauma to tissue and a reduced inflammatory response.

Once the cannula 100, and in particular opening 110, is properly positioned within the patient, the method may proceed to step 408, where fat or other biocompatible filler materials, e.g., dermal filler, may be injected into patient tissue adjacent to the implant. The physician may inject the fat or dermal filler into the body of the patient by manual or pump-assisted mechanisms described above. In at least one example, the physician may move the cannula 100 in a back-and-forth or in-and-out movement pattern similar to the action used in evacuating fat during liposuction. In at least one example, fat (or other biocompatible material) is not inserted into the submuscular or subglandular pocket where the implant is located, but instead into the surrounding subglandular or subcutaneous tissue, e.g., including the natural fat layer. Fat may be inserted into a single location or multiple locations in the surrounding or nearby tissue(s). A typical fat transfer procedure may proceed in less than about 30 minutes, e.g., from about 5 to about 15 minutes, although other suitable procedure times also are contemplated depending on the nature of the refinement desired or required. In some examples, no introduction device (e.g., an introduction scope or sheath) is used at any point during the procedure, although, in some examples, such an introduction device could be used. The total volume of fat injected during the procedure may range from about 5 mL to about 500 mL, such as from about 5 mL to about 50 mL, from about 5 mL to about 100 mL, from about 100 mL to about 500 mL, or from about 50 mL to about 250 mL. For example, the procedure may include injecting from 5 mL to 100 mL of fat in one or more locations adjacent to a right breast implant and/or 5 mL to 100 mL of fat in one or more locations adjacent to a left breast implant.

The distal tip 108 of cannula 100 may come into contact with the outer surface of a breast implant at various times during steps 406 and/or 408. The shape and configuration of cannula 100 may help to prevent damage to the breast implant. For example, cannula 100 may be configured to apply at least 10 N of force, or from about 1 N to about 40 N of force, to the implant without puncturing or otherwise compromising the integrity of the implant shell. The breast implant may have characteristics that comply with the applicable medical regulations (e.g., shell thickness, shell elasticity, filling material viscosity, implant shape, implant volume, etc.), including the exemplary shell thicknesses, shell elongation values, and gel elasticity (penetration) values discussed above. Thus, for example, cannula 100 may be configured to apply at least 10 N of force, e.g., from about 10 N to about 40 N, from about 20 N to about 40 N, or from about 20 N to about 30 N, e.g., at least 20 N, at least 25 N, or at least 30 N of force without puncturing or otherwise compromising the integrity of the implant shell.

Generally, thicker shells have more resistance to sustaining damage, such as rupture, by a cannula. However relatively thin shells (e.g., having a thickness of 1.2 mm or less, or 1.0 mm or less) may be desired or preferred, e.g., as being more similar to natural tissue or better able to simulate natural tissue. The atraumatic tip shape of cannulas of the present disclosure helps avoid contact between the shell and the opening/injection hole when cannula 100 is pressed against the implant shell. For relatively thin implant shells, the atraumatic tip may be especially helpful to avoid punctures, tears, or other damage to the implant.

Similarly, the implant may be configured to receive a force of at least about 10 N from the distal tip 108 of cannula 100 without rupturing or puncturing. In some examples, the implant may be configured to receive a force of at least about 25 N, at least about 35 N, or at least about 50 N without rupturing or puncturing the implant.

Thus, the distal tip 108 may be disposed directly in contact with the surface of the implant during various points of the procedure, and may deliver fat or other biocompatible material(s) into the patient while applying a force against the surface of the implant. When injecting materials into the patient tissue, for example, the distal tip 108 may be disposed between about 0.1 mm and about 30 mm from the outer surface of the implant, e.g., from about 0.1 mm and about 10 mm, or from about 0.5 mm and about 1 mm. In some examples, the distal end 106 of cannula 100 may be in contact with the outer surface of the implant before, during, or after injection. The method may include injecting fat into one, two, three, or more different locations at different areas around the implant, including, e.g., subcutaneous space where fat is normally located. Therefore, fat may be injected into the natural fat layer. In case of a previous breast implant and subsequent presence of a capsule, the injected fat may be placed between the capsule and the skin. For example, the fat may be injected proximal or distal to the implant, above or below the implant, or to the side of the implant. The volume of fat or other material(s) injected may range from about 5 mL to about 500 mL, e.g., about 50 mL, about 100 mL, or about 150 mL.

The following examples are intended to illustrate aspects of the present disclosure without, however, being limiting in nature. It is understood that the present disclosure encompasses additional embodiments consistent with the foregoing description.

EXAMPLES

Studies were done to evaluate the performance characteristics of cannulas of the present disclosure for comparison to existing fat grafting cannula devices. For these tests, a Tensile Tester (Instron) was used to apply force with each cannula device and record the amount of force applied to different breast implants. The Tensile Tester uses pneumatic, mechanical and electronic systems to transmit measurement data to a computer. The cannulas used in these studies were fixed with the upper grip of the Tensile Tester (see FIGS. 5 and 6). The studies were configured in the equipment software to provoke the cannula to penetrate the implant, and register the force applied. The distance that the cannulas pressed into the implants was found to be dependent upon the implant type, and its orientation in the Tensile Tester relative to the cannula.

Example 1

A first compression test was performed using three types of cannulas (cannulas 1-3) to apply force against six different silicone gel filled implants (implants 1-6). Cannulas 1-3 were each stainless steel having an ovoid, bulbous shaped tip. Cannulas 1 and 2 each had lengths of 120.0 mm, outer diameters of 1.60 mm, with rounded rectangular openings having a length dimension of 2.50 mm, and a width dimension of 1.20 mm. The distance from the distalmost tip of cannulas 1 and 2 to the edges of the respective openings (the length Y+C in FIG. 1) was 5.5 mm. Cannula 3 had a length of 150.0 mm, an outer diameter of 2.10 mm, with a rounded rectangular opening having a length dimension of 3.20 mm, and a width dimension of 1.60 mm. The distance from the distalmost tip of cannula 3 to the opening (the length Y+C in FIG. 1) was 7.9 mm.

The implants tested were Motiva Implants® (Establishment Labs S.A.) with a shell thickness between 0.0130 inches (~0.33 mm) and 0.022 inches (~0.56 mm). Implants 1-3 were Motiva Ergonomix™ SilkSurface™ implants comprising a textured silicone shell of thickness 0.0130 inches to 0.022 inches (5 layers of silicone dispersion) and enclosing a silicone gel with a penetration value of 50-60$\frac{1}{10}$ mm. Implants 4-6 were Motiva SilkSurface™ PLUS implants comprising a textured silicone shell of thickness 0.0130 inches to 0.040 inches (6 layers of silicone dispersion) and enclosing a silicone gel with a penetration value of 20-35$\frac{1}{10}$ mm. The silicone gel used in implants 1-3 had an elasticity that allowed the projection of the implants to shift in response to gravity, simulating movement of natural tissue. As indicated by the lower penetration value, the silicone gel used in implants 4-6 had somewhat greater cohesion, such that the gel of implants 4-6 was less responsive to gravity. The implant volumes for implants 1 and 4 were 925 mL, for implants 2 and 5 were 375 mL, and for implants 3 and 6 were 105 mL.

Figure 5:
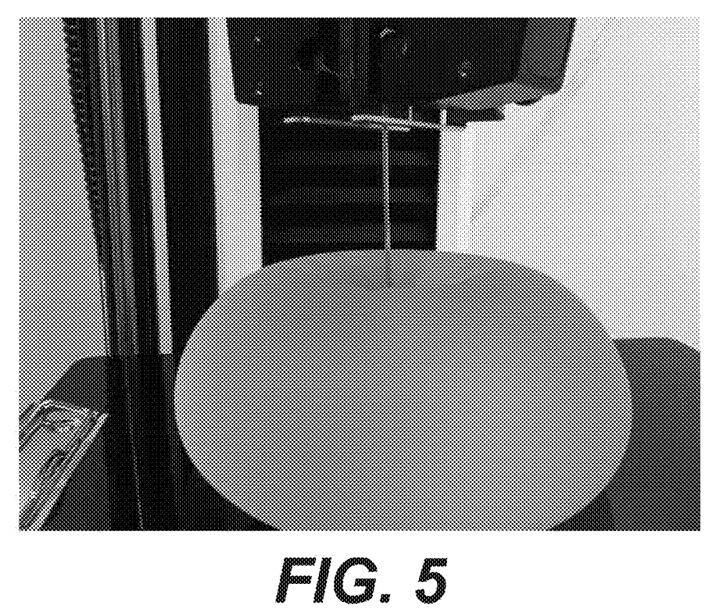
FIGS. 5 and 6 are photographs from studies described in Examples 1 and 2 placing exemplary cannulas of the present disclosure in contact with breast implants.
Figure 6:
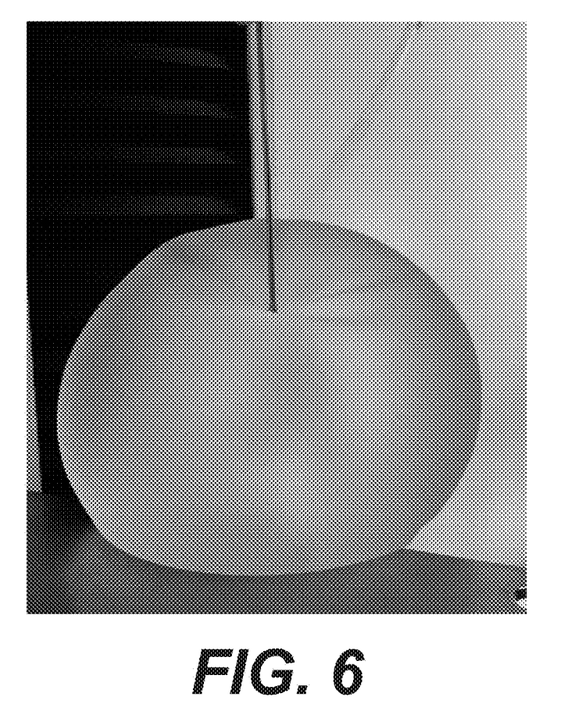
Figure 9:
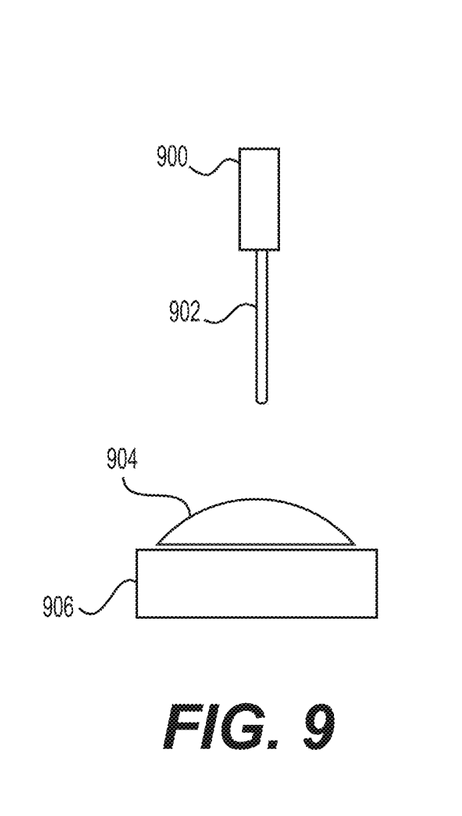
FIGS. 9-11 are schematic illustrations of a testing procedure described in Examples 1 and 2.
Figure 10:
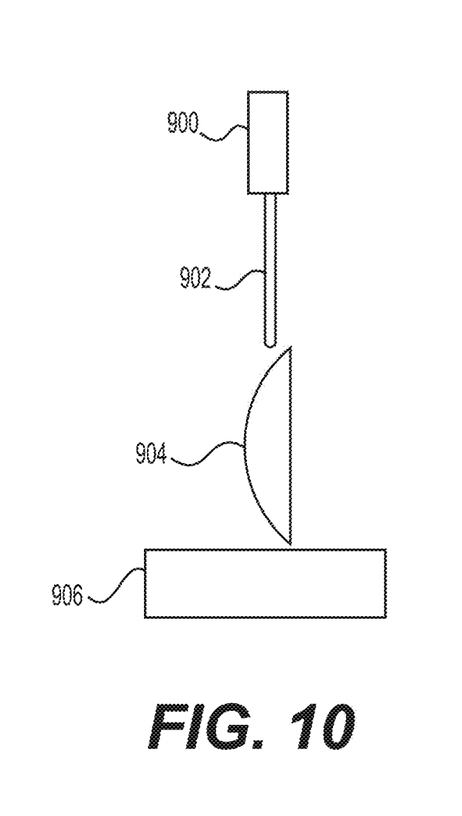
Figure 11:
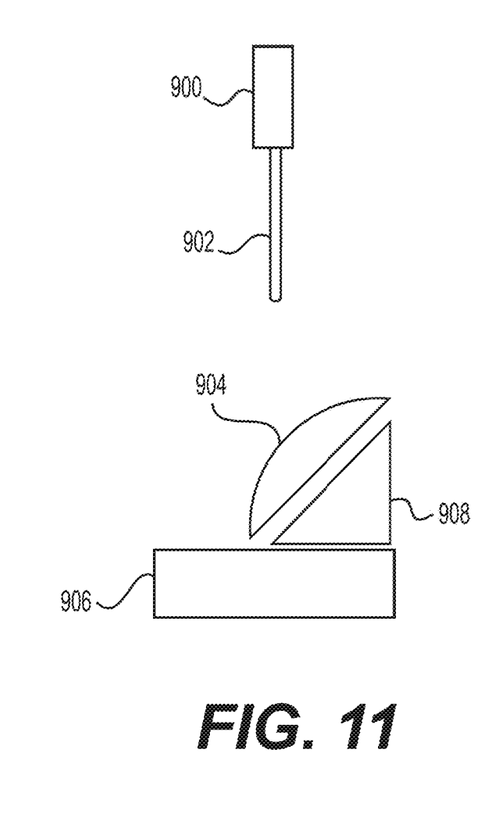

The compression test was executed under various parameters (e.g., implant penetration distance, implant volume, and orientation within the Tensile Tester, e.g., 0 degrees, 45 degrees, and 90 degrees—shown in FIGS. 9-11) to identify under which conditions a rupture of an implant may occur upon contact with a cannula. As shown in FIGS. 5 and 6, and illustrated in FIGS. 9-11, the study was performed by placing each implant 904 in horizontal, vertical, and angled orientations on a flat surface (e.g., base 906 shown schematically in FIGS. 9-11). For each orientation, the cannula 902 was placed in the upper grip 900 of the Tensile Tester and advanced towards the implant 904 to contact the implant surface, and the amount of force applied to the implant 904 via the cannula 902 was gradually increased. In a horizontal position at 0 degrees (see FIG. 9), the cannula 902 advanced along the projection of implant 904, perpendicular to base 906. At 45 degrees (see FIG. 11), the implant 904 was supported on a plate 908 with a 45 degree angle, and the cannula 902 advanced from the apex of implant 904 towards base 906. In a vertical position at 90 degrees (see FIG. 10), the cannula 902 advanced along the total base diameter of implant 904.

Testing was carried out as follows. To start, each cannula 902 was placed in the upper grip 900 of the tensile tester with the distal end of the cannula 902 almost touching the surface of implant 904. Before initiating the test, the distance from the cannula distal end to the base 906 below the implant 904 was measured by removing the implant 904 and manually moving the upper grip 900 with the cannula 902 to the base 906, and recording the distance. After this distance was obtained, the cannula 902 was moved back to its initial position, and the tensile tester was configured to travel the measured distance. During the test, the tensile tester moves the upper grip 900 downwards, enabling the cannula 902 to push down on the outer surface of the implant 904. As this downward movement occurs, the tensile tester records the force applied against upper grip 900 (i.e., the resistance of the implant 904).

In these tests, the force was not increased manually by the operator, as the process is preconfigured to measure the resistance of each implant, and record the maximum force applied (maximum resistance). For the cannulas that did not rupture the implant, this maximum was found to occur when the cannulas reached above 95% of the penetration distance. For the cannulas that caused a rupture of the implant (see Example 2 below), the maximum force occurred at the point before the cannula pierced or ruptured the implant.

Figure 7:
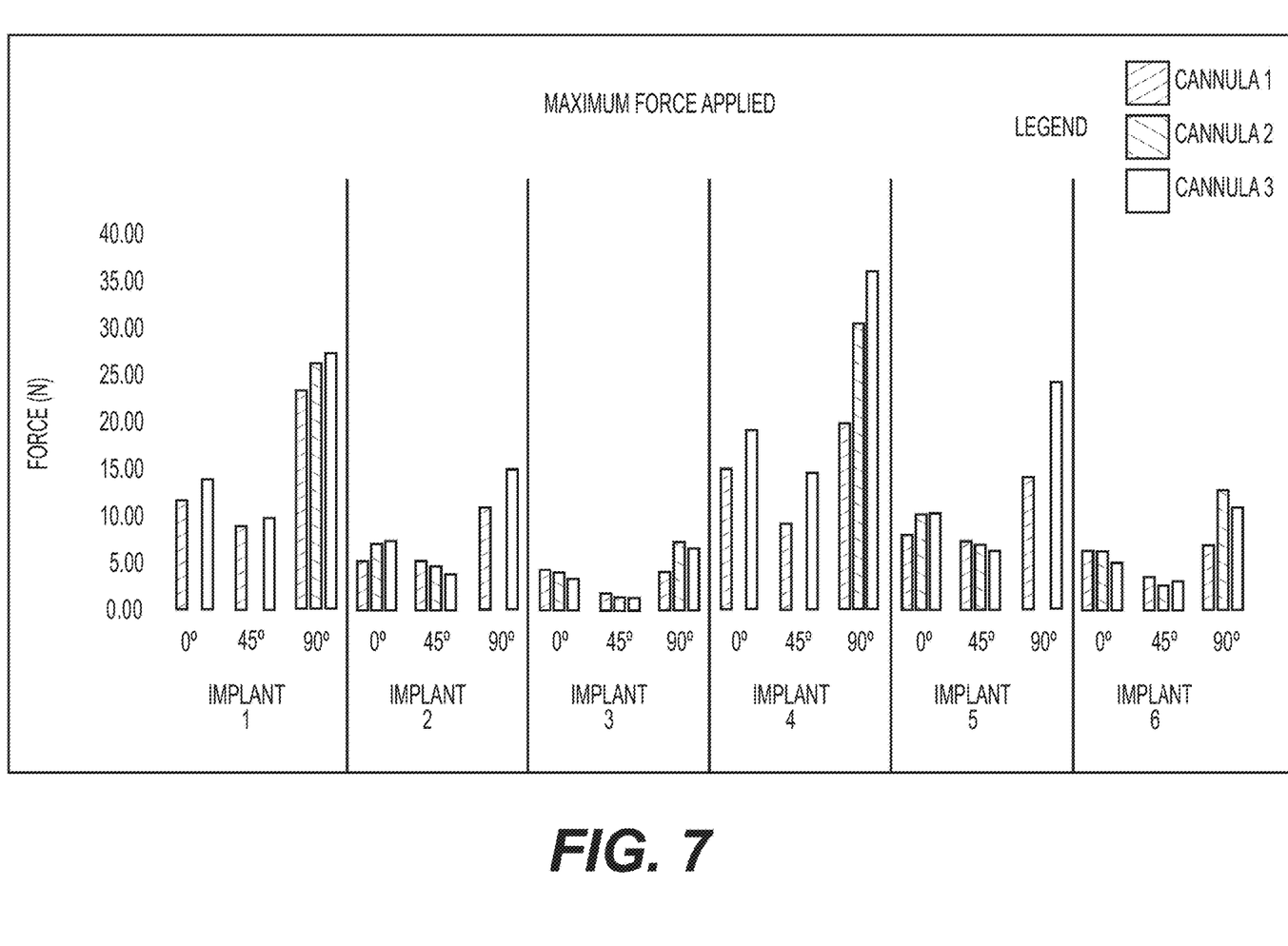
FIG. 7 is a graph illustration of the results of a study described in Example 1.

Results for cannulas 1-3 having an atraumatic distal tip are shown in FIG. 7. Maximum resistance of each implant to the force applied by the cannula was registered as maximum force by the Tensile Tester sensors. This force tended to increase for implants with higher volumes, for example, implants 1 and 4, or when the traveling distance of the cannula increased. For example, at 90 degrees (see FIG. 10), more gel is between the cannula and the base than in any other orientation. The force applied by cannula 3 was generally higher than the force applied by cannulas 1 and 2. This was understood to result from the larger outer diameter of cannula 3 (2.10 mm) as compared to the outer diameter of cannulas 1 and 2 (1.60 mm). Thus, the bulbous shape tip of cannula 3 was also larger, resulting in more surface contact and resistance between cannula 3 and the implants. It was also found that implants 1-3 having a less cohesive silicone gel (such that the gel was more responsive to gravity to simulate movement of natural tissue) had higher values of maximum force applied by the cannulas, which may be due to the ability of the gel to deform around the cannula as it pressed against the implant surface.

No ruptures were observed. The various distal tips of cannulas 1-3, regardless of size or the position in which the cannulas were pressed against the implants, did not penetrate the outer shells of the implants. Instead, the distal tip pushed gently against the surface of the implant and the deformation of the implant did not impede or block the opening in the cannula.

Cannulas 1 and 2 were identical. Because of their relatively thin width, cannulas 1 and 2 tended to bend when compressed against the implants of higher volume (375 mL and 925 mL). That is, rather than release the pressure against the implants by puncturing the implant, the cannulas bent. In one case, cannula 2 bent so severely that it became unsuitable for further testing. Results for cannula 2 are therefore not shown in FIG. 7 for some orientations of implants 1, 2, 4, and 5. Cannulas 1 and 3 were used to collect data for each of implants 1-6 in all three orientations.

Further testing of cannulas 1-3 has shown that upwards of 35 N or more of compression force can be sustained without damage to the implants. The distal tips of cannulas 1-3 were found to be capable of pressing into the surface of the implants at a distance approximately equal to the diameter of the base (see FIG. 11), or the projection height of the implants (see FIG. 9), without damaging the implants.

Example 2

Figure 8:
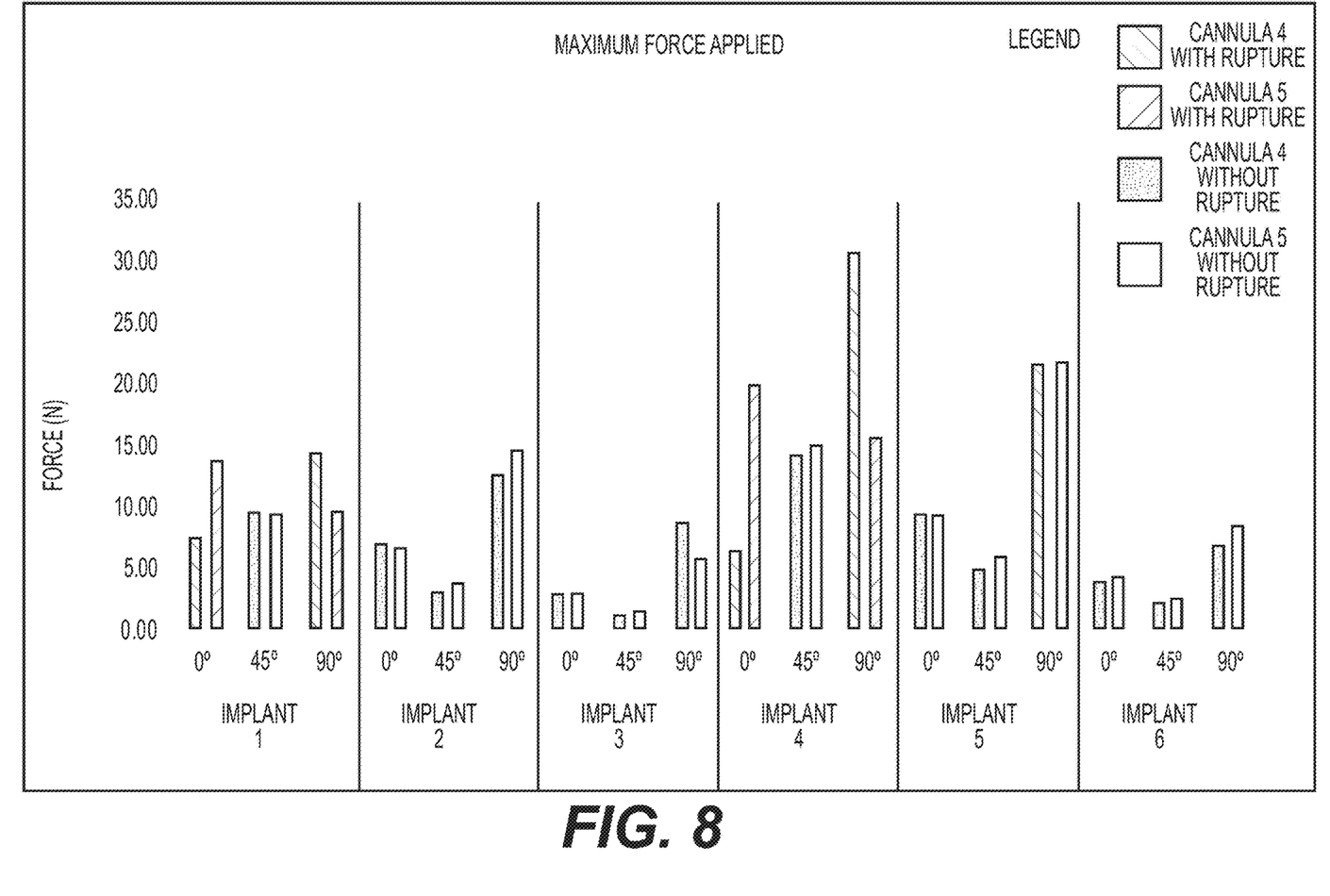
FIG. 8 is a graph illustration of the results of a study described in Example 2.

In a separate compression test, the results of which are shown in FIG. 8, two comparison fat grafting devices (cannulas 4 and 5) without a bulbous tip were tested against implants 1-6 under similar conditions as in Example 1. These comparison fat grafting devices were formed of stainless steel. Cannula 4 had a length of 120.0 mm, an outer diameter of 1.65 mm, an inner diameter of 1.36 mm, an opening having a length A of 2.6 mm and a width B of 1.1 mm (see FIG. 1), and a length of 4.2 mm from a distal end of its opening to a distalmost tip of the cannula. Cannula 5 had a length of 150.0 mm, an outer diameter of 2.11 mm, an inner diameter of 1.7 mm, an opening having a length A of 3.3 mm and a width B of 1.3 mm (see FIG. 1), and a length of 2.7 mm from a distal end of its opening to a distalmost tip of the cannula.

It was found that 27% of the cases in this comparison test failed, causing ruptures among the implant shells. The comparison fat grafting devices, although having rounded tips, included an exposed injection hole relatively close to the ends of the cannulas. The sharp edges of the holes caused ruptures and/or tears of the implant shell when pressed against the implant when sufficient force was applied through the cannulas.

Any aspect or feature in any embodiment may be used with any other embodiment set forth herein. It will be apparent to those skilled in the art that various modifications and variations can be made in the disclosed implants, implant features, and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

We claim:

1. A method treating a patient, the method comprising:
   inserting a cannula into tissue adjacent to a breast implant, the cannula including:
   a member having a lumen therein;
   an atraumatic, ovoid, distal tip having a maximum diameter ranging from about 3 mm to about 4 mm; and
   an opening disposed proximal to the distal tip, the opening being in fluid communication with the lumen and having a length ranging from 2.2 mm to 2.7 mm and a width ranging from 1.0 mm to 1.5 mm;

wherein inserting the cannula includes directly contacting a shell of the breast implant without puncturing the breast implant, the shell having a thickness of less than 1.0 mm and enclosing a silicone gel; and delivering fat, autologous to the patient, through the member and the opening, into the tissue.

2. The method of claim 1, further comprising:

creating an umbilical, axillary, breast fold, or areolar incision in the patient; and delivering the breast implant to a submuscular or subglandular pocket via the incision;

wherein the cannula is inserted into the tissue via the incision after delivering the breast implant.

3. The method of claim 2, wherein the fat is not delivered into the submuscular or subglandular pocket that contains the breast implant.

4. The method of claim 1, wherein the member of the cannula has an outer diameter ranging from 1.5 mm to 2.5 mm.

5. A method treating a patient, the method comprising:

creating an umbilical, axillary, breast fold, or areolar incision in the patient;

delivering a breast implant to a submuscular or subglandular pocket via the incision;

inserting a cannula into tissue adjacent to the breast implant, the cannula including:

a member having a lumen therein, the member having an outer diameter ranging from 2.0 mm to 2.5 mm and an inner diameter ranging from 1.0 mm to 1.5 mm;

an atraumatic, ovoid, distal tip having a maximum diameter greater than the outer diameter of the member; and an opening disposed proximal to the distal tip, the opening being disposed in a circumferential side surface of the member and in fluid communication with the lumen;

wherein inserting the cannula includes directly contacting a shell of the breast implant without puncturing the breast implant, the shell having a thickness ranging from 0.3 mm to 0.6 mm and enclosing a silicone gel; and delivering fat, autologous to the patient, through the member and the opening, into the tissue, wherein the fat is not delivered into the submuscular or subglandular pocket that contains the breast implant.

* * * * *